United States Patent [19]

Yang et al.

[11] 4,097,535

[45] Jun. 27, 1978

[54] PREPARATION OF ALDEHYDES FROM ALCOHOLS

[75] Inventors: Kang Yang; Kaye L. Motz; James D. Reedy, all of Ponca City, Okla.

[73] Assignee: Continental Oil Company, Ponca City, Okla.

[21] Appl. No.: 763,958

[22] Filed: Jan. 31, 1977

[51] Int. Cl.² ............................................. C07C 45/16
[52] U.S. Cl. ................................................ 260/603 C
[58] Field of Search ........................... 260/603 C, 606

[56] References Cited

U.S. PATENT DOCUMENTS

| | | | |
|---|---|---|---|
| 3,959,383 | 5/1976 | Northeimer | 260/603 C |
| 3,987,107 | 10/1976 | McClellan et al. | 260/603 C |

*Primary Examiner*—James O. Thomas, Jr.
*Assistant Examiner*—Werren B. Lone
*Attorney, Agent, or Firm*—Bayless E. Rutherford, Jr.

[57] ABSTRACT

An improved method of preparing an aldehyde by passing alcohol and air through a reactor containing a silver catalyst is disclosed. Briefly, the improvment comprises passing the alcohol and air through a zone, packed with silver catalyst, maintained at subreaction temperature prior to passing the reactants through the reaction zone. In a preferred embodiment, the reactants, after leaving the reaction zone, are passed through a zone containing inert material and maintained at a subreaction temperature.

7 Claims, No Drawings

PREPARATION OF ALDEHYDES FROM ALCOHOLS

BACKGROUND

There are many uses for aliphatic aldehydes. For example, the $C_8$–$C_{14}$ aldehydes have pleasant odors and are used in perfumes. In addition, the aldehydes can be converted to amines or acids, which have many commercial uses. For example, ethylamine is used in petroleum refining to form complex cuprous chloride salts for the recovery of diolefins.

A conventional method of preparing an aldehyde is to pass a combination of alcohol and air through a reactor packed with metallic salt or silver-impregnated catalyst. This method has the following disadvantages: (1) a conversion above 90% at above 90% selectivity is not attainable and (2) when the alcohol has a high boiling point, e.g. dodecyl alcohol, sub-atmospheric pressure must be used to vaporize the alcohol.

Our invention is directed to an improvement in the above-described method of preparing aldehydes.

PRIOR ART

A search of the prior art did not produce any references teaching the specific process of our invention.

An article by Darris and Hodgson in *J. Chem. Soc.*, 282 (1943) teaches the catalytic dehydrogenation of alcohols to aldehydes in the presence of air using a variety of catalysts including silver or copper gauze. This process has been discussed in the "Background" section.

BRIEF SUMMARY OF THE INVENTION

Briefly stated, the present invention is directed to an improvement in the method of preparing aldehydes from alcohols by passing alcohol and an oxygen-containing gas over silver catalyst at an elevated temperature wherein the improvement comprises first passing the alchol and oxygen-containing gas through a pre-reactor zone, containing silver catalyst, said zone being at a temperature lower than that of the reaction zone.

In a preferred embodiment the improvement comprises the additional step of passing the reactants through a post-reactor zone containing inert material and being at a sub-reaction temperature

DETAILED DESCRIPTION

Materials Used

Suitable alcohols for our process include primary alcohols containing from 1 to 30 carbon atoms. The alcohols can be straight or branched-chain. The preferred alcohols contain from 5 to 15 carbon atoms. The process is suitable for use with mixtures of alcohols or a single alcohol.

At the risk of being redundant it is noted that the alcohol is converted to the corresponding aldehyde. For example, a $C_{10}$ alcohol is converted to a $C_{10}$ aldehyde.

Suitable oxygen-containing gases include oxygen per se, air, oxygen-nitrogen mixtures, and air-nitrogen mixtures. In addition to nitrogen other inert gases can be used in combination with the oxygen-containing gas.

The amount of oxygen-containing gas, based on the oxygen content, used is in the range of from about 0.1 to about 10 moles oxygen per mole of alcohol. On the same basis the preferred amount of oxygen-containing gas is from about 0.5 to about 5 moles.

Typically, the silver catalyst used is in the form of wire or screen. Other forms of silver such as very small pellets can also be used.

The amount of alcohol to catalyst is related to the weight hourly space velocity (WHSV), which also defines reaction time $$WHSV = \frac{\text{weight of alcohol per hour}}{\text{weight of catalyst}}$$

A suitable range of WHSV is about 0.1 to about 100 with a preferred range being about 1 to about 10.

Any finely-divided inert material can be used in the post-reaction zone. Examples of suitable inert materials include glass wool, glass beads, sand, and fine gravel.

Process Conditions

There are at least two, preferably three, zones through which the reactants pass in our process. The intermediate zone, which is referred to as the reaction zone, contains silver catalyst and is maintained at a higher temperature (e.g. above 300° C. to about 600° C.). There is a zone before the reaction zone which is referred to as pre-reactor zone. This zone contains silver catalyst and is maintained at a temperature below that employed in the reactor zone. The temperature should be at least 50° below that in the reaction zone. A suitable temperature range is from about 25° C. to 50° below maximum reaction zone temperature. The preferred temperature range is from about 25° C. to 300° C., with the additional limitation that the maximum temperature is at least 50° below the reaction zone temperature. In a preferred embodiment there is a zone after the reactor zone which is referred to as post-reactor zone. This zone is packed with an inert material and is maintained at a temperature range corresponding to that employed for the pre-reactor zone. (The temperature ranges are the same — not the temperatures). We wish to emphasize that since excellent results are obtained using the lower temperature ranges there is seldom any necessity for operating outside this range.

The zone and conditions therein can be summarized as follows:

| Zone | Packing | Temperature |
|---|---|---|
| Pre-Reactor | silver | about 25–300° C** |
| Reactor | silver | 300–about 600° C |
| Post-Reactor* | inert material | about 25–300° C** |

*Preferred embodiment only
**Preferred range - Also, the maximum range is at least 50° below the reactor temperature The temperature in the various zones is controlled by applying external heat to the various zones. For example, in the laboratory, electrical heating tape is placed around the entire apparatus to control the temperature of the various zones.

Our process results in a conversion of at least 90%, with a selectivity of at least 85%, more usually at least 90%.

In order to illustrate the nature of the present invention still more clearly, the following examples will be given. It is to be understood, however, that the invention is not to be limited to the specific conditions or details set forth in these examples except insofar as such limitations are specified in the appended claims.

EXAMPLE 1

This example illustrates need for having silver catalyst in the pre-heater. The alcohol used was 1-octanol. A 2 cm I.D. Pyrex tube 40 cm long equipped with an 8 mm thermowell placed in the center of the tube and running lengthwise was filled with about 3.5 g of silver screen in approximately the center of the tube and glass beads above and below the catalyst. Five thermocouples were spaced through the reactor to indicate the temperature in the preheat zone; the front, middle, and last parts of the catalyst zone, and in the post catalyst section. The reaction tube was placed in a resistance furnace which was inclined about 15° from horizontal. The 1-octanol was pumped into the preheater by means of a metering pump and was mixed then with the oxidizing gas mixture. The products were collected in a vented ice-cooled trap. Analyses were by gas chromatograph. The run conditions and results are shown below.

| Run No. | Alcohol Feed Rate ml/hr | Silver Catalyst | GAS Air ml/min | GAS N₂ ml/min | TEMPERATURE Pre-heat °C | TEMPERATURE Catalyst °C | TEMPERATURE Post-Cat °C | Conv % | Select % | Acid % |
|---|---|---|---|---|---|---|---|---|---|---|
| A | 120 | Screen 1 g | 800 | 1000 | 385 | 458 | 385 | 60 | 89 | 1.8 |
| B | 120 | Screen 1 g | 800 | 1000 | 365 | 500 | 417 | 66 | 94 | 2.4 |
| C | 30 | Wool 5 g | 300 | 1000 | 193 | 290 | 270 | 27 | 98 | — |
| D | 30 | Wool 15 g | 300 | 1000 | 253 | 400 | 332 | 58 | 97 | — |
| E | 30 | Wool 15 g | 200 | 1000 | 388 | 500 | 435 | 48 | 95 | — |
| F | 120 | Needles 26 g | 800 | 1000 | 426 | 503 | 310 | 49 | 95 | — |
| G | 120 | Needles 26 g | 800 | 1000 | 410 | 537 | 372 | 62 | 86 | — |

EXAMPLE 2

This example illustrates the invention. It shows the need for having the pre-reactor zone and the advantage of the post-reactor zone.

The alcohols used were octanol and dodecanol. The alcohols were fed directly to the tube which contained one or more of the following zones:
(a) Reactor zone alone
(b) Reactor zone + pre-reactor zone
(c) Reactor zone + pre-reactor zone + post-reactor zone The reactor used was a Pyrex tube (0.8 cm I.D.) in which 0.4 O.D. Pyrex thermocouple well was axially placed. The reaction zone, 8 cm long, was packed with 4.5 g of silver wool obtained from Fisher Scientific Co. (Fair Lawn, N.J.). The reaction temperature was controlled by adjusting current through a heating tape wrapped around the reaction zone. In some runs, the reaction zone was preceded by a 3 cm-long, loosely-packed silver wool (at room temperature). Also, in some runs, additionally the reaction zone was followed by 3 cm-long loosely-packed glass wool (at room temperature). Other experimental conditions were as follows:

Liquid alcohol feed rate = 0.229 cc/min.
Air Feed rate = 120 cc/min.
Temperature profile in the reaction zone:

| Distance from top, cm | 1 | 2 | 3 | 4 | 5 | 6 |
|---|---|---|---|---|---|---|
| Temp. (with alcohol) °C | 462 | 492 | 509 | 512 | 505 | 484 |
| Temp. (no alcohol) °C | 413 | 453 | 485 | 490 | 475 | 442 |

The results are summarized in Table 1.

Table I
Conversion of Alcohols to Corresponding Aldehydes

| Alcohol | Zones Used in Process* | Conversion, % | Selectivity, % |
|---|---|---|---|
| Octanol | A | 77 | 91 |
| Octanol | B | 93 | 90 |
| Octanol | C | 96 | 93 |
| Dodecanol | A | 57 | 88 |
| Dodecanol | B | 91 | 88 |
| Dodecanol | C | 96 | 91 |

A = Reactor zone alone
B = Reactor zone + pre-reactor zone
C = Reactor zone + pre-reactor zone + post-reactor zone Thus, having described the invention in detail, it will be understood by those skilled in the art that certain variations and modifications may be made without departing from the spirit and scope of the invention as defined herein and in the appended claims.

We claim:
1. In the method of preparing $C_5$–$C_{15}$ aldehydes from primary $C_5$–$C_{15}$ alcohols by passing alcohol and an oxygen containing gas over silver catalyst at an elevated temperature the improvement comprising passing a the alcohol and an oxygen-containing gas through a pre-reactor zone, containing silver catalyst, and being at a temperature in the range of about 25° to about 300° C., and then passing the reactants through the reaction zone which is at a temperature of above 300° C. to about 600° C., said pre-reactor zone having a maximum temperature of at least from about 25° to 50° C. below the reaction zone temperature, said improved process being characterized further as providing a conversion of at least 90% with a selectivity of at least 85%.

2. The method of claim 1 wherein the improvement comprises the additional step of passing the alcohol and oxygen-containing gas through a post-reactor zone packed with inert material and maintained at a temperature in the range of about 25° to about 300° C. and having a maximum temperature of about 25° to 50° C. below the reaction zone temperature.

3. The method of claim 1 wherein the oxygen to alcohol ratio is in the range of about 0.1 to about 10 moles of oxygen per mole of alcohol.

4. The method of claim 3 wherein the amount of alcohol to catalyst, expressed as weight hourly space velocity, is in the range of about 0.1 to about 100.

5. The method of claim 4 wherein the oxygen-containing gas is oxygen, air, air-nitrogen mixtures, or oxygen-nitrogen mixtures.

6. The method of claim 5 wherein the improvement comprises the additional step of passing the alcohol and oxygen-containing gas through a post-reactor zone maintained at a temperature in the range of about 25° to about 300° C. and having a maximum temperature of about 25° to 50° C. below the reactor temperature.

7. The method of claim 6 wherein
(a) the oxygen to alcohol ratio is in the range of about 0.5 to about 5 moles of oxygen per mole of alcohol, and
(b) the amount of alcohol to catalyst, expressed as weight hourly space velocity is in the range of about 1 to about 10.

* * * * *